United States Patent [19]

Schaar

[11] 4,062,362
[45] Dec. 13, 1977

[54] DISPOSABLE AND SELF ADJUSTABLE DIAPERS

[75] Inventor: Charles H. Schaar, Lake Zurich, Ill.

[73] Assignee: Colgate-Palmolive Company, New York, N.Y.

[21] Appl. No.: 644,699

[22] Filed: Dec. 29, 1975

[51] Int. Cl.² .............................................. A61F 13/16
[52] U.S. Cl. ...................................... 128/287; 128/284
[58] Field of Search ................... 128/290 P, 284, 287, 128/290 R, 296, 286

[56] References Cited

U.S. PATENT DOCUMENTS

| 3,071,138 | 1/1963 | Garcia | 128/290 R |
| 3,364,931 | 1/1968 | Hirsch | 128/290 R |
| 3,444,859 | 5/1969 | Kalwaites | 128/284 |
| 3,545,441 | 12/1970 | Gravdahl | 128/284 |
| 3,570,492 | 3/1971 | Bettencourt | 128/290 R |
| 3,669,114 | 6/1972 | Morane | 128/290 R |
| 3,888,257 | 6/1975 | Cook | 128/296 |
| 3,954,107 | 5/1976 | Chesky | 128/290 R |

FOREIGN PATENT DOCUMENTS 21,764 of 1902 United Kingdom ................ 128/284

Primary Examiner—Aldrich F. Medbery
Attorney, Agent, or Firm—Powell L. Sprunger

[57] ABSTRACT

A disposable diaper comprising, an absorbent pad assembly having a backing sheet, a top sheet, a pair of side edges, a pair of end edges, and a plurality of longitudinally extending absorbent pads disposed in a contiguous relationship laterally across the pad assembly between the backing sheet and the top sheet. Adjoining pads of the pad assembly are longitudinally separated along a line extending between end edges of the pads and through the thickness of the pads to permit relative longitudinal movement of opposed lateral side margins of the pad assembly.

10 Claims, 4 Drawing Figures

DISPOSABLE AND SELF-ADJUSTABLE DIAPERS

BACKGROUND OF THE INVENTION

The present invention relates to absorbent articles, and more particularly to disposable diapers.

In recent years, diapers of the disposable type have come into widespread use due to convenience of parents, since such diapers may be discarded after a single use. Although in many respects satisfactory for their intended purpose, certain problems remain with the diapers. Such diapers are normally constructed from a fluid impervious backing sheet, a fluid pervious top sheet, and an absorbent pad intermediate the backing and top sheets which extends between sides of the diapers. It has been found that when such diapers are placed on an infant, the absorbent pad serves to limit relative longitudinal movement between opposed lateral margins of the diaper. The sides of such diapers bind against the infant's legs and thus limit freedom of movement of the legs causing discomfort to the infants.

SUMMARY OF THE INVENTION

A principal feature of the present invention is the provision of a disposable diaper of simplified construction which provides greater comfort to the infant.

The diaper of the present invention comprises, an absorbent pad assembly having a backing sheet, a top sheet, a pair of side edges, a pair of end edges, and a plurality of longitudinally extending absorbent pads disposed in a contiguous relationship laterally across the pad assembly between the backing sheet and top sheet. Adjoining pads of the pad assembly are longitudinally separated along a line extending between end edges of the pads and through the thickness of the pads.

A feature of the present invention is that the separate pads permit relative longitudinal movement of opposed lateral side margins of the pad assembly.

Another feature of the present invention is that the separate pads thus minimize binding of the infant's legs by the diaper when worn and permits greater leg movement without discomfort to the infant.

Yet another feature of the invention is that the separate pads may have different densities to obtain desired fluid holding capacities and absorption rates which vary in the different pads.

Still another feature of the invention is that different pads may include hydrophilic and hydrophobic absorbent pad portions to obtain varying fluid holding capacities in the separate pads under loads.

Further features will become more fully apparent in the following description of the embodiments of this invention and from the appended claims.

DESCRIPTION OF THE PREFERRED EMBODIMENTS

Figure 1:
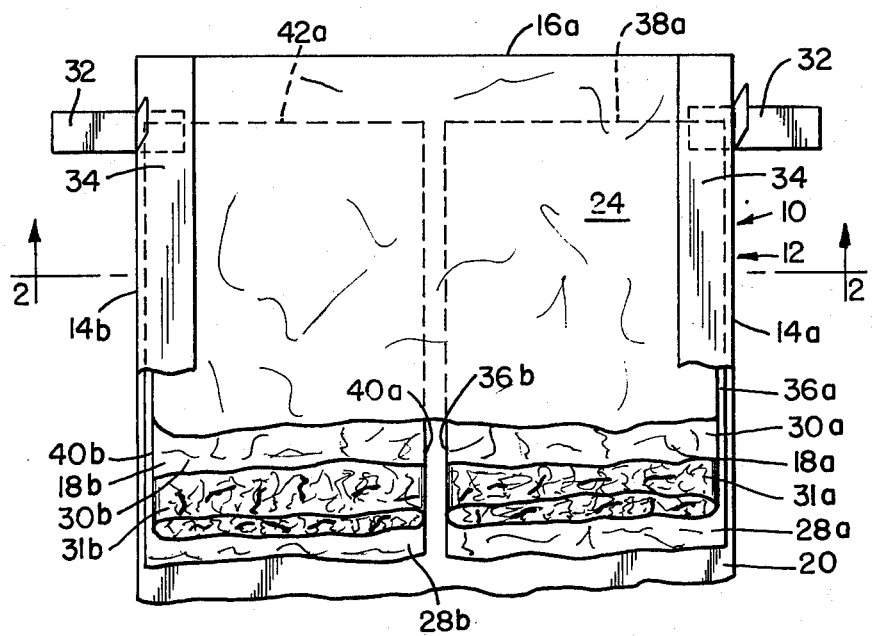
FIG. 1 is a fragmentary plan view of a disposable diaper of the present invention.
Figure 2:
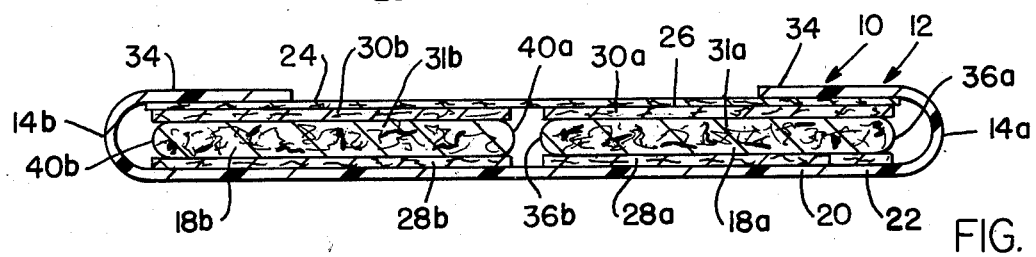
FIG. 2 is a sectional view taken substantially as indicated along the line 2—2 of FIG. 1.

Referring now to FIGS. 1 and 2, there is shown a disposable diaper generally designated 10 having an absorbent pad assembly 12. The pad assembly 12 has a pair of side edges 14a and 14b, and a pair of end edges 16a and 16b connecting the side edges 14a and b. The pad assembly 12 also has a pair of elongated absorbent pads 18a and 18b, a fluid impervious backing sheet 20, such as polyethylene, covering a back surface 22 of the pads 18a and b, and a fluid pervious top sheet 24, such as a nonwoven material, covering a front surface 26 of the pads 18a and b. Each of the pads 18a and b may have a respective back wadding sheet 28a and 28b, a front wadding sheet 30a and 30b, and an absorbent pad portion or filler 31a and 31b, such as wood fluff, positioned between the respective back and front wadding sheets 28a and b and 30a and b, as shown. The diaper 10 may also have a pair of tape fasteners 32 for securing the diaper about an infant during placement of the diaper, and the backing sheet 20 may have lateral side margins 34 folded over and secured to the front of the pad assembly.

Figure 3:
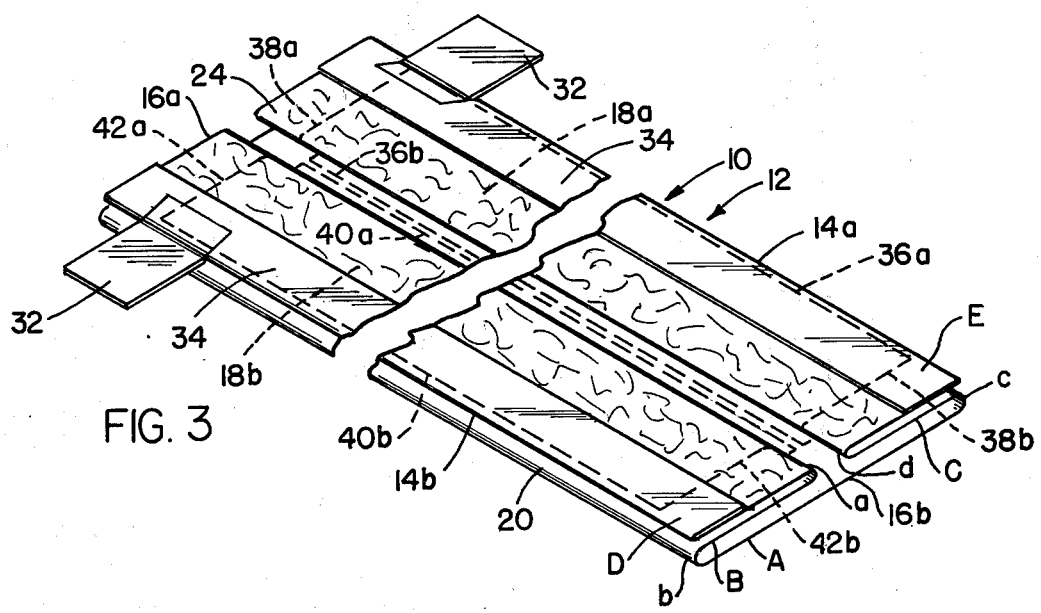
FIG. 3 is a fragmentary perspective view of the diaper of FIG. 1 as folded into a box-pleat configuration.

With reference to FIGS. 1–3, the absorbent pad 18a has a pair of side edges 36a and 36b, and a pair of end edges 38a and 38b connecting the side edges 36a and b. Similarly, the absorbent pad 18b has a pair of side edges 40a and 40b, and a pair of end edges 42a and 42b connecting the side edges 40a and b. As shown, the outer side edge 36a of the pad 18a and the outer side edge 40b of the pad 18b are preferably located adjacent the side edges 14a and 14b of the pad assembly 12, respectively, such that the pads extend laterally in the pad assembly substantially between the side edges 14a and b of the pad assembly. Also, the end edges 38a and b of the pad 18a and the end edges 42a and b of the pad 18b are preferably spaced from the end edges 16a and 16b of the absorbent pad assembly 12. As shown, the pads 18a and b are separated in the lateral central region of the pad assembly along a line which extends between the end edges of the pads adjacent the inner side edges 36b and 40a of the pads 18a and b, respectively. Accordingly, the pads are disposed in a contiguous or side-by-side relationship laterally across the pad assembly while being separated through the thickness of the pads between the backing sheet 20 and the top sheet 24. The back and front surfaces of the pads 18a and b are preferably attached by adhesive to the backing sheet and top sheet.

Since the absorbent pads are detached from each other, the pads permit relative longitudinal movement of the pad assembly between the pads and relative longitudinal movement of opposed lateral side margins of the pad assembly adjacent the side edges 14a and b during use of the diaper. When the diaper is secured about the infant, one lateral side margin of the diaper is permitted to move relative the other lateral side margin of the diaper without impediment by a unitary absorbent pad, which would conventionally extend completely across the diaper. Thus, the pad assembly minimizes binding of the infant's legs by the diaper and permits a greater degree of leg movement without discomfort to the infant during use of the diaper.

As illustrated in FIG. 3, the flat diaper of FIG. 1 may be folded along a plurality of longitudinally extended fold lines a, b, c, and d to define a box-pleat configuration of the diaper 10. The box-pleat diaper has a longitudinally extending central panel A, a pair of first pleat panels B and C extending from and overlying the central panel A, and a pair of outermost pleat panels D and E extending from and overlying the first pleat panels B and C.

Figure 4:
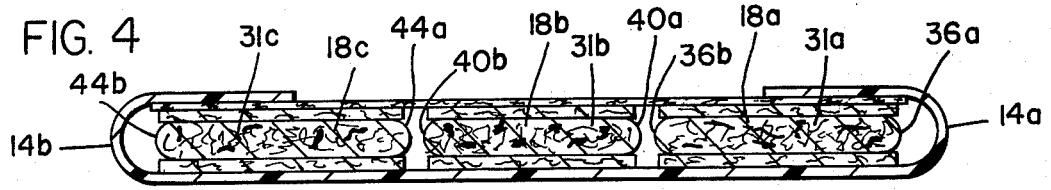
FIG. 4 is a sectional view of another embodiment of a disposable diaper of the present invention.

Another embodiment of the diaper of the present invention is illustrated in FIG. 4, in which like reference numerals designate like parts. In this embodiment, the pad assembly 12 has a longitudinally extending central pad 18b and a pair of side pads 18a and 18c located intermediate the central pad 18b and the side edges 14a and b of the pad assembly 12. As before, the pads 18a, b, and c may have front and back wadding sheets and an absorbent pad portion between the wadding sheets, as shown. The adjoining pads 18a and 18b are separated along a line extending between end edges of the pads at the respective side edges 36b and 40a, while the adjoining pads 18b and 18c are separated along a longitudinally extending line adjacent the respective side edges 40b and 44a, as shown. Thus, the diaper of FIG. 4 permits relative longitudinal movement of opposed lateral side margins of the pad assembly for added comfort to the infant, as described in connection with the diaper of FIGS. 1–3.

If desired, the absorbent pad portions 31a, b, and c of the respective pads 18a, b, and c may comprise sections of wood fluff, as previously described. However, in one embodiment, the pad portions 31a, b, and c may have different densities to obtain an improved diaper for dispersing and retaining fluids. In a preferred form, the central pad portion 31b has a greater density than the side pad portions 31a and 31c, which may be achieved by compressing the pad portion 31b to a greater extent than the pad portions 31a and c. In this configuration, the densified central pad portion 31b provides a relatively high rate of fluid absorption and transmission, such that urine passing through the diaper top sheet 24 is rapidly absorbed and transmitted to the side pads 18a and 18c by the central pad 18b. Also, since the pad portions 18a and c are less dense than the pad portion 31b, the pad portions 31a and c have larger interfiber spacings resulting in greater fluid holding capacity in the pad portions 31a and c than in the pad portion 31b. Thus, in this embodiment of the diaper, the dense central pad 18b rapidly transmits urine to the less dense side pads 18a and 18c where the urine is retained during later use of the diaper.

In another embodiment of the diaper of the present invention, the pad portion of one of the pads may comprise a mass of hydrophilic fibers while the pad portion of another pad may comprise a mass of hydrophobic fibers. With reference to FIG. 4, in one form the central pad portion 31b may be composed of a hydrophilic central material, such as cellulosic fibers, while the side pad portions 31a and c may be composed of hydrophobic fibers such as polyolefins, polyesters, acrylics, polyvinyls, polyamides, or various mixtures thereof. In this embodiment, the fibers in pad portions 31a and c have a greater wet resiliency and thus maintain their interfiber spacings open to a greater extent when wetted and placed under loads. Accordingly, the pad portions 31a and c of the side pads 18a and c display relatively high fluid holding capacities when the diaper is wetted and placed under loads, such that a relatively large quantity of urine is retained adjacent sides of the diaper during use. The pad portion 31b of the central pad 18b may be made relatively dense, in order that the pad 18b absorbs and transmits urine at a rapid rate to the side pads 18a and c for retention therein, as previously described.

It will be apparent that any number of pads may be used in the diaper of the present invention. Also, the side edges between adjoining pads may be abutting or spaced, or side margins of the pads may be slightly overlapped, if desired.

The foregoing detailed description is given for clearness of understanding only, and no unnecessary limitations should be understood therefrom, as modifications will be obvious to those skilled in the art.

I claim:

1. A disposable diaper comprising, an absorbent pad assembly having a backing sheet, a top sheet, a pair of side edges and a plurality of separate longitudinally extending absorbent pads disposed in a side-by-side relationship laterally across the pad assembly between said backing sheet and top sheet, means to permit relative longitudinal movement of opposed lateral side margins of said pad assembly comprising locating said pads in the pad assembly with adjoining sides of the pads being longitudinally separated and movable along a line extending between end edges of the pads and through the thickness of the pads.

2. The diaper of claim 1 wherein said pads extend laterally in the pad assembly substantially between the side edges of the pad assembly.

3. The diaper of claim 1 wherein said pad assembly has a pair of separate pads.

4. The diaper of claim 3 wherein said pair of pads are separated adjacent the lateral central region of the pad assembly.

5. The diaper of claim 1 wherein said pad assembly has a central pad and a pair of said pads located intermediate the central pad and the side edges of the pad assembly.

6. The diaper of claim 1 wherein each of said pads includes a back wadding sheet, a front wadding sheet, and an absorbent pad portion between said back and front wadding sheets.

7. A disposable diaper comprising, an absorbent pad assembly having a backing sheet, a top sheet, a pair of side edges, and absorbent pads means comprising a plurality of longitudinally extending absorbent pad portions disposed in a side-by-side relationship laterally across the pad assembly, with at least one of said pad portions having a greater density of fibers than another of said pad portions with said pad portions being longitudinally separated and movable along their adjacent edges to permit relative movement of the opposed lateral side margins of said pad assembly.

8. The diaper of claim 7 wherein said pad means has a relatively dense central pad portion, and a pair of side pad portions intermediate said central pad portion and the side edges of the pad assembly, with said pad portions being less dense than said central pad portion.

9. A disposable diaper comprising, an absorbent pad assembly having a backing sheet, a top sheet, a pair of side edges, and absorbent pad means comprising a plurality of longitudinally extending separate absorbent pad portions disposed in a side-by-side relationship laterally across the pad assembly, with at least one of said pad portions comprising a mass of hydrophilic fifbers and another of said pad portions comprising a mass of hydrophobic fibers with said pad portions being longitudinally separated and movable along their adjacent edges to permit relative movement of the opposed lateral side margins of said pad assembly.

10. The diaper of claim 9 wherein said pad means has a central pad portion composed of hydrophilic fibers, and a pair of side pad portions composed of hydrophobic fibers located intermediate said central pad portion and the side edges of the pad assembly.

* * * * *